United States Patent
Park et al.

(10) Patent No.: US 10,254,268 B2
(45) Date of Patent: Apr. 9, 2019

(54) METHOD FOR DETECTING TOXIC METAL IONS IN SAMPLE

(71) Applicant: Korea University Research and Business Foundation, Sejong Campus, Sejong-si (KR)

(72) Inventors: Jinsung Park, Seoul (KR); Woong Kim, Gwangju (KR); Joohyung Park, Seoul (KR); Seongjae Jo, Seoul (KR); Minwoo Kim, Guri-Si (KR); Gyudo Lee, Seoul (KR)

(73) Assignee: Korea University Research and Business Foundation, Sejong Campus, Sejong-si (KR)

( * ) Notice: Subject to any disclaimer, the term of this patent is extended or adjusted under 35 U.S.C. 154(b) by 114 days.

(21) Appl. No.: 15/465,344

(22) Filed: Mar. 21, 2017

(65) Prior Publication Data

US 2017/0307581 A1   Oct. 26, 2017

(30) Foreign Application Priority Data

Mar. 22, 2016   (KR) .......................... 10-2016-0033951

(51) Int. Cl.

| | |
|---|---|
| *G01N 33/20* | (2019.01) |
| *G01N 1/28* | (2006.01) |
| *B82Y 30/00* | (2011.01) |
| *B82Y 35/00* | (2011.01) |
| *C01G 7/00* | (2006.01) |
| *G01Q 60/24* | (2010.01) |
| *G01Q 60/28* | (2010.01) |
| *G01N 21/78* | (2006.01) |
| *G01Q 60/30* | (2010.01) |
| *G01N 15/00* | (2006.01) |
| *B82Y 15/00* | (2011.01) |

(52) U.S. Cl.
CPC .............. *G01N 33/20* (2013.01); *B82Y 30/00* (2013.01); *B82Y 35/00* (2013.01); *C01G 7/00* (2013.01); *G01N 1/28* (2013.01); *G01N 21/78* (2013.01); *G01Q 60/24* (2013.01); *G01Q 60/30* (2013.01); *B82Y 15/00* (2013.01); *G01N 2015/0038* (2013.01)

(58) Field of Classification Search
CPC ......... B82Y 15/00; B82Y 30/00; B82Y 35/00; C01G 7/00; G01N 1/28; G01N 2015/0038; G01N 21/78; G01N 33/20; G01Q 60/24; G01Q 60/30
USPC ........................................ 436/73, 80, 81, 89
See application file for complete search history.

(56) References Cited

U.S. PATENT DOCUMENTS

| | | | | |
|---|---|---|---|---|
| 2015/0111790 | A1* | 4/2015 | Ategeka | A61B 5/14546 506/39 |
| 2016/0327473 | A1* | 11/2016 | Ozcan | G01N 33/1813 |
| 2017/0038303 | A1* | 2/2017 | Lee | G01N 21/80 |

FOREIGN PATENT DOCUMENTS

KR   10-2016-0023759   *   3/2016

OTHER PUBLICATIONS

Chen et al. Analyst, vol. 137, 2012, pp. 2021-2023.*
Bui et al. Analytical Bioanalytical Chemistry, vol. 388, 2007, pp. 1185-1190.*
Sener et al. ACS Applied Materials & Interfaces, vol. 6, Oct. 20, 2014, pp. 18395-18400.*
Kim et al. Sensors and Actuators B: Chemical, vol. 255, Sep. 7, 2017, pp. 2179-2186.*

* cited by examiner

*Primary Examiner* — Maureen Wallenhorst
(74) *Attorney, Agent, or Firm* — NSIP Law

(57) ABSTRACT

Disclosed is a method for detecting toxic metal ions in a sample. The method includes: a) preparing a solution of organic acid-bound gold nanoparticles; b) adding a sample containing toxic metal ions to the solution prepared in a) to allow the gold nanoparticles to aggregate; c) dropping the reaction solution obtained in b) onto a silicon substrate and drying the reaction solution such that the gold nanoparticle aggregates are immobilized on the silicon substrate; and d) analyzing the characteristics of the gold nanoparticles immobilized on the silicon substrate. The method enables the detection of even a trace amount of toxic metal ions in a sample with high sensitivity. Therefore, the method can be applied to the management of water quality in food service providers and hospitals, the measurement of contaminants in water supply and drainage systems, and the management of industrial wastewater. Furthermore, the method is expected to be widely applicable to water purifiers and the food and beverage industry in the future.

11 Claims, 15 Drawing Sheets

METHOD FOR DETECTING TOXIC METAL IONS IN SAMPLE

CROSS-REFERENCE TO RELATED APPLICATIONS

This application claims priority to Korea Patent Application No. 10-2016-0033951, filed Mar. 22, 2016, the disclosure of which is incorporated herein by reference.

BACKGROUND OF THE INVENTION

1. Field of the Invention

The present invention relates to a method for detecting toxic metal ions in a sample.

2. Description of the Related Art

Various kinds of metals, such as aluminum, mercury, silver, copper, chromium, cobalt, and copper, have been reported to adversely affect human health when accumulated in the human body through the food chain from secondary and tertiary consumers.

Particularly, aluminum is a representative metal element for industrial and household applications and is useful in various fields. Generally, aluminum itself does not appear to adversely affect human health due to its low abundance ($\sim 10^{-15}$ M) in primary consumers in nature. It was however reported that aluminum adversely affects various human tissues, including bone, brain, liver, heart, spleen, and muscle, when accumulated through the food chain. Under these circumstances, there is a need for sensors capable of maintaining the concentration of aluminum at a constant level. In addition, early detection of aluminum ions not only in wastewater treatment facilities but also in food service providers and medical institutions, including health centers and hospitals, is very important for public health.

In this connection, a research group led by Shan C. et al. reported visual detection of aluminum ion in citrate capped gold nanoparticles in sample (Shan C. "Rapid visual detection of aluminum ion using citrate capped gold nanoparticles". 2012. Analyst). This research proposed a method for detecting aluminum ions ($Al^{3+}$) in a sample based on a phenomenon in which the addition of aluminum ions to a solution of citrate-coordinated gold nanoparticles changes the color of the solution from red to blue.

However, according to the above method, the lowest concentration of aluminum ions detectable using an optical instrument is only about 1 µM. That is, the detection performance of the method is limited

SUMMARY OF THE INVENTION

The present invention has been made in an effort to solve the problems of the prior art. Specifically, the present invention is intended to provide a technique for accurately and selectively detecting even a trace amount of toxic metal ions present in a sample based on the difference in surface potential between before and after organic acid-bound gold nanoparticles are bound with the toxic metal ions.

One aspect of the present invention provides a method for detecting toxic metal ions in a sample, including: a) preparing a solution of organic acid-bound gold nanoparticles; b) adding a sample containing toxic metal ions to the solution prepared in a) to allow the gold nanoparticles to aggregate; c) dropping the reaction solution obtained in b) onto a silicon substrate and drying the reaction solution such that the gold nanoparticle aggregates are immobilized on the silicon substrate; and d) analyzing the characteristics of the gold nanoparticles immobilized on the silicon substrate.

According to one embodiment of the present invention, the organic acid may be selected from the group consisting of citric acid, cytosine, thymine, and mixtures thereof.

According to a further embodiment of the present invention, the toxic metal ions may be ions of at least one metal selected from the group consisting of aluminum, mercury, silver, and copper.

According to another embodiment of the present invention, the characteristics of the gold nanoparticles may be the height and surface potential of the gold nanoparticle aggregates.

According to another embodiment of the present invention, the height of the gold nanoparticle aggregates may be measured by atomic force microscopy.

According to another embodiment of the present invention, the surface potential of the gold nanoparticle aggregates may be measured by Kelvin probe force microscopy.

According to another embodiment of the present invention, the gold nanoparticles may be allowed to aggregate at room temperature for 1.5 hours to 3 hours.

The method of the present invention enables the detection of even a trace amount of toxic metal ions in a sample with high sensitivity. Therefore, the method of the present invention can be applied to the management of water quality in food service providers and hospitals, the measurement of contaminants in water supply and drainage systems, and the management of industrial wastewater. Furthermore, the method of the present invention is expected to be widely applicable to water purifiers and the food and beverage industry in the future.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 3a shows solutions of HAuCl4 and TSC immediately after the addition of aluminum sample solutions containing aluminum ions at different concentrations of 1 pM, 10 pM, 100 pM, 1 nM, 10 nM, 100 nM, 25 µM, 37.5 µM, 50 µM, and 100 µM from the left, and FIG. 3b shows the mixture solution at 12 h post-addition;

DETAILED DESCRIPTION OF THE INVENTION

The present invention will now be described in more detail.

The present inventors intended to detect toxic metal ions present in a sample based on the aggregation between the toxic metal ions and organic acid-bound gold nanoparticles and to detect the toxic metal ions with high sensitivity or detectability by analyzing particular characteristics of the gold nanoparticle aggregates formed on a substrate.

The present invention provides a method for detecting toxic metal ions in a sample, including: a) preparing a solution of organic acid-bound gold nanoparticles; b) adding a sample containing toxic metal ions to the solution prepared in a) to allow the gold nanoparticles to aggregate; c) dropping the reaction solution obtained in b) onto a silicon substrate and drying the reaction solution such that the gold nanoparticle aggregates are immobilized on the silicon substrate; and d) analyzing the characteristics of the gold nanoparticles immobilized on the silicon substrate.

Figure 1:
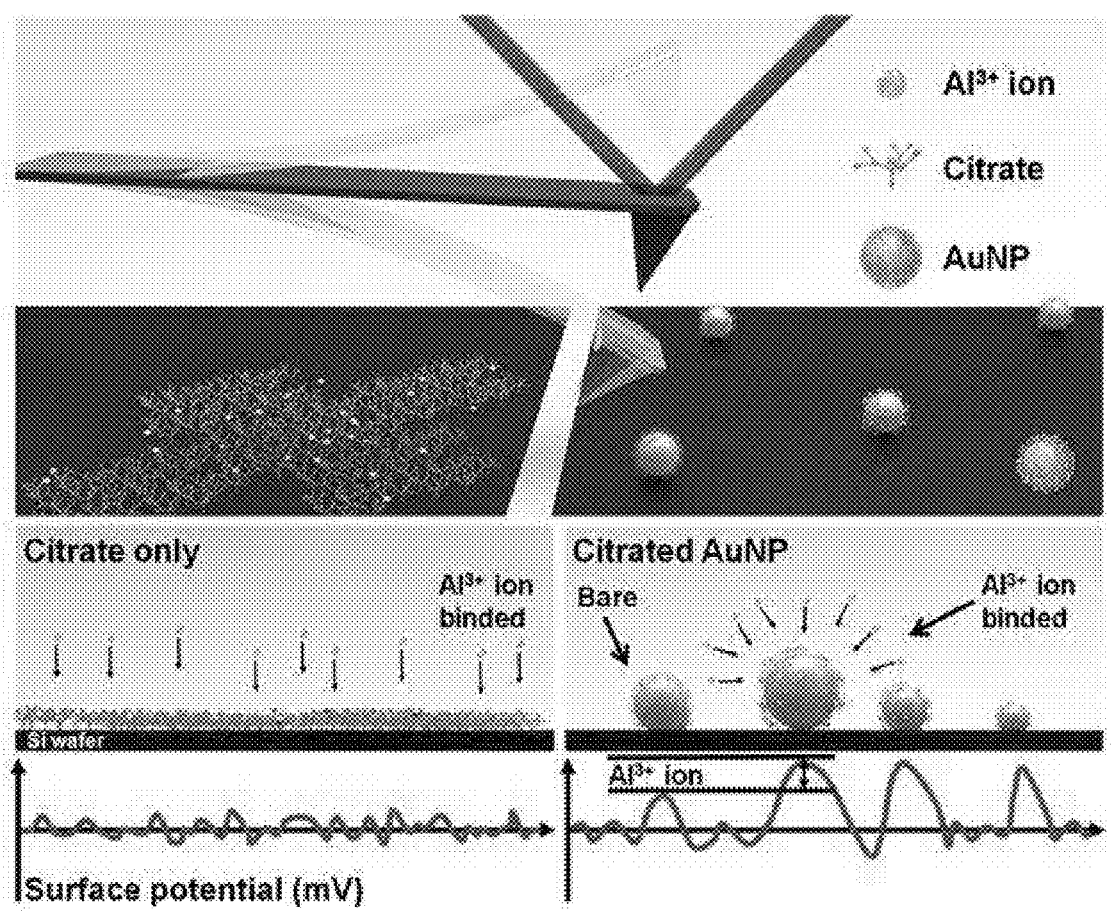
FIG. 1 is a conceptual diagram showing a method for detecting toxic metal ions according to the present invention.

FIG. 1 is a conceptual diagram showing the method of the present invention. The method of the present invention will be explained below with reference to FIG. 1. First, an organic acid is bound to the surface of gold nanoparticles to prepare a solution of organic acid-bound gold nanoparticles. Any suitable organic acid that can be bound to the surface of the gold nanoparticles may be used in the method of the present invention. For example, the organic acid may be selected from the group consisting of citric acid, cytosine, thymine, and mixtures thereof.

The organic acid may be, for example, citric acid. In this case, a solution of HAuCl4 as a precursor of the gold nanoparticles is mixed with a solution of trisodium citrate (TSC) and the resulting mixture is heated for a predetermined time to prepare a solution of organic acid-bound gold nanoparticles.

Alternatively, the organic acid may be cytosine or thymine. In this case, nucleotides end-capped with thiol groups are dissolved in Tris-EDTA buffer and the solution is allowed to react with a solution of gold nanoparticles at room temperature for 2 hours to prepare a solution of cytosine- or thymine-bound gold nanoparticles in DNA.

Next, a sample containing toxic metal ions as analytes is added to the solution prepared in a). As a result, the toxic metal ions aggregate with the organic acid-bound gold nanoparticles. In the Examples section that follows, aluminum ions were used as the toxic metal ions. However, the toxic metal ions are not necessarily limited to aluminum ions and other metal ions may be used according to how the gold nanoparticles are coated. For example, the toxic metal ions may be ions of at least one metal selected from the group consisting of aluminum, mercury, silver, and copper.

The gold nanoparticles may be allowed to aggregate at room temperature for 1.5 hours to 3 hours. If the aggregation time is less than 1.5 hours, sufficient aggregation of the gold nanoparticles with the toxic metal ions is not expected. Meanwhile, if the aggregation time exceeds 3 hours, it takes a long time for analysis.

Subsequently, the reaction solution obtained in b) is dropped onto a silicon substrate and dried such that the gold nanoparticle aggregates are immobilized on the silicon substrate. The material for the substrate is not necessarily limited to silicon and any suitable substrate for atomic force microscopy and Kelvin probe force microscopy may be used in the method of the present invention. Examples of other suitable substrate materials include glass and plastic materials.

Finally, the characteristics of the gold nanoparticles immobilized on the silicon substrate are analyzed so that the presence of the toxic metal ions in the analyte sample can be detected. Particularly, the height and surface potential of the gold nanoparticle aggregates can be analyzed. The method of the present invention has high detection sensitivity compared to the color analysis by visual observation or spectroscopy according to the method of Shan C. et al. For example, the height of the gold nanoparticle aggregates may be measured by atomic force microscopy and the surface potential of the gold nanoparticle aggregates may be measured by Kelvin probe force microscopy. Kelvin probe force microscopy is at least 1000 more sensitive for detection than existing color analysis methods. In addition, the method of the present invention is based on high binding force between gold nanoparticles and aluminum ions. According to the method of the present invention, the location of aluminum ions can be easily determined using gold nanoparticles compared to using small monomolecular organic acids. Due to their high electrical conductivity, gold nanoparticles are electrically amplified compared to monomolecular organic acids, enabling more sensitive surface potential analysis when bound with aluminum ions (FIG. 1).

The present invention will be more specifically explained with reference to the following examples. However, these examples are provided to assist in understanding the invention and do not serve to limit the scope of the invention.

Test Methods 1.00 g of trisodium citrate (TSC) was mixed with 99.00 g of water to prepare a 1% TSC solution. Separately, 100 mL of distilled water and a stirring bar were placed in a 250 mL beaker, followed by heating in a water bath. When the water temperature reached 90° C. or higher, 1 mL of 1% HAuCl4 and 5 mL of the 1% TSC were sequentially added to the beaker. The color change of the solution was observed under heating for 30 min. The beaker was removed from the water bath, wrapped with an aluminum foil, and cooled for 30 min. Five vials were filled with the solution (each 2 mL).

$Al(ClO_4)_3 \cdot 9H_2O$ as a precursor of gold nanoparticles was added in different amounts to 10 mL of DW to prepare sample solutions having concentrations of $10^{-4}$ M, $5 \times 10^{-4}$ M, $10^{-5}$ M, and $5 \times 10^{-5}$ M. For the solution preparation, the precursor was completely dissolved by vortexing.

The four of the five vials were filled with the aluminum ion-containing sample solutions (each 1 mL) and the remaining one was filled with 1 mL of DW. Moving pictures were taken to monitor the color changes. After the lapse of a sufficient time, changes of the solutions were observed.

Figure 2:
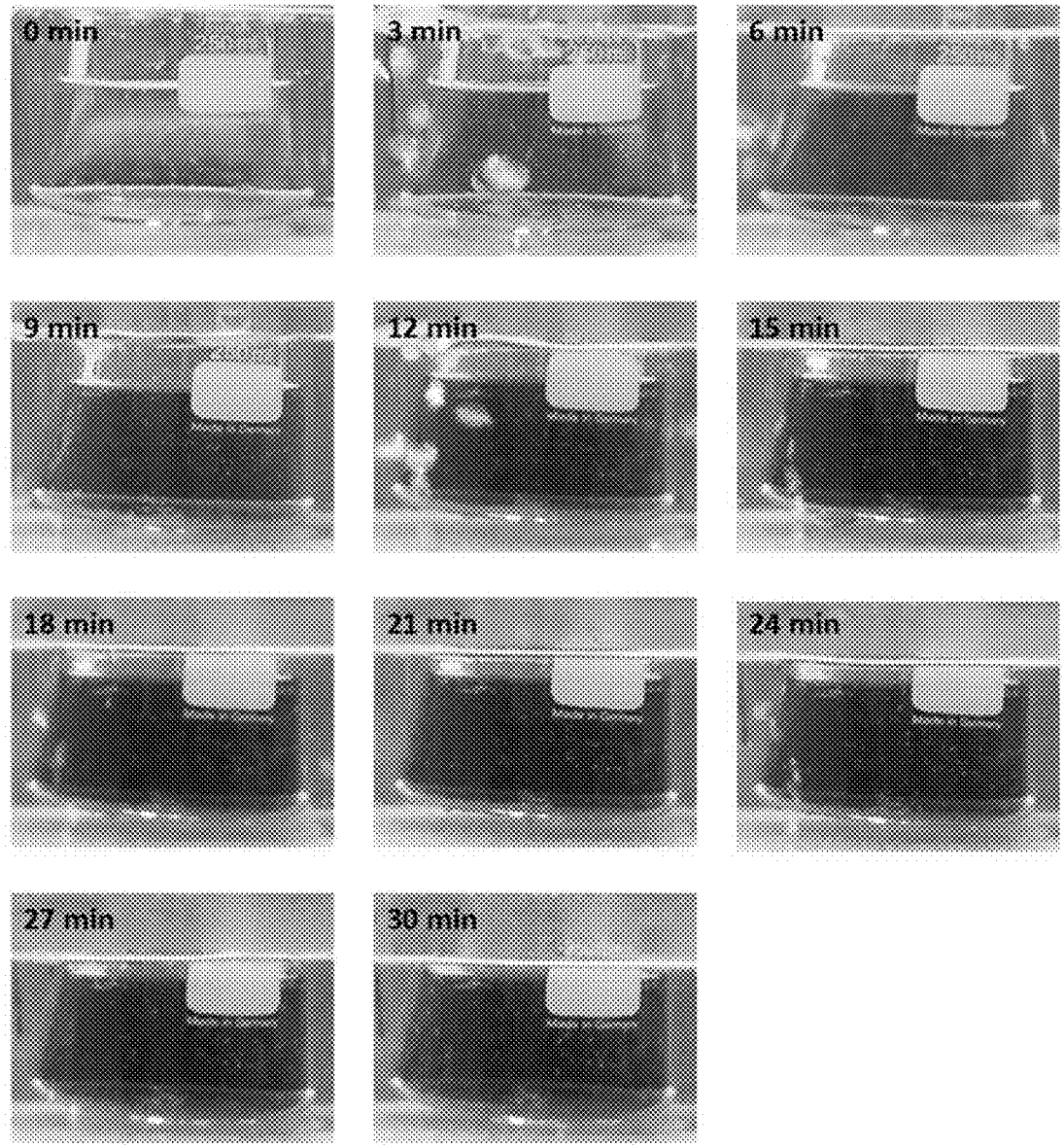
FIG. 2 shows changes in the color of a solution of 1 ml of 1% HAuCl4 and 5 ml of 1% TSC under heating for 30 minutes, which were imaged every three minutes.

Changes in the Color of the Solution According to the Formation of Gold Nanoparticles FIG. 2 shows changes in the color of the solution of 1 ml of 1% HAuCl4 and 5 ml of 1% TSC under heating for 30 minutes. Images were taken every three minutes.

Referring to FIG. 2, as the heating time increased, the solution turned red. This color change demonstrates the formation of gold nanoparticles in the solution. This is attributed to the reduction of gold ions to gold by the reaction with the citric acid and the action of the citrate as a stabilizer to form aggregates of the gold particles.

Figure 3A:
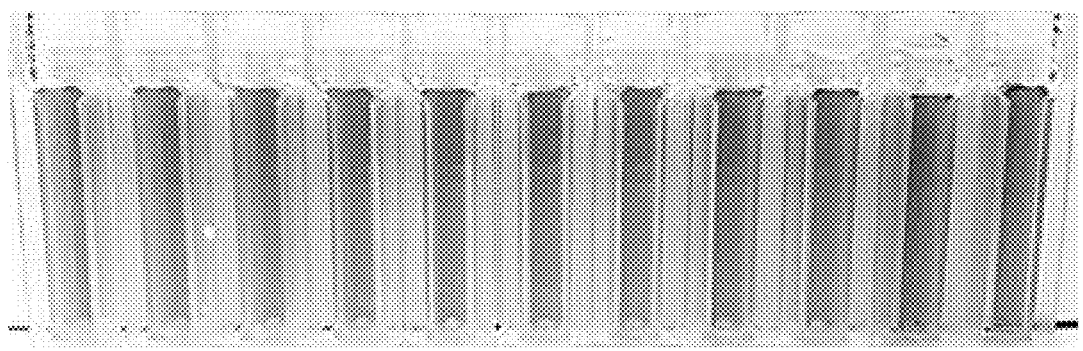
FIGS. 3a and 3b.
Figure 3B:

Changes in the Color of Samples Containing Aluminum Ions at Different Concentrations (1) As described above, 1 ml of DW and sample solutions containing aluminum ions at different concentrations of 1 pM, 10 pM, 100 pM, 1 nM, 10 nM, 100 nM, 25 μM, 37.5 μM, 50 μM, and 100 μM were added to solutions containing HAuCl4 and TSC and their color change were observed. FIG. 3a shows the solutions of HAuCl4 and TSC immediately after the addition of the aluminum sample solutions and FIG. 3b shows the mixture solution at 12 h post-addition.

Referring to FIG. 3a, immediately after the addition of each sample solution containing aluminum ions, the color of the mixture solution turned from red to blue. The color of the mixture solution turned darker blue with increasing concentration of aluminum ions. FIG. 3b shows the mixture solution after the addition of the sample solution containing aluminum ions. Referring to FIG. 3b, the solution become transparent. However, a precise examination of the solution shown in FIG. 3b revealed that small black particles floated in the solution. This indicates that the aluminum particles sufficiently reacted with the gold nanoparticles, resulting in an increase in the size of the gold particles, and as a result, the color of the solution was no longer colored and instead the gold particle aggregates were observed in the form of small black particles by the naked eye.

(2) In addition, aluminum ions at concentrations of 100 μM to 1 pM were allowed to react with the citrated gold nanoparticles (the solution containing HAuCl4 and TSC) in a 1:1 ratio. The reaction products were observed by the naked eye and UV-VIS spectroscopy.

Figures 4A, 4B, 4C, 4D:
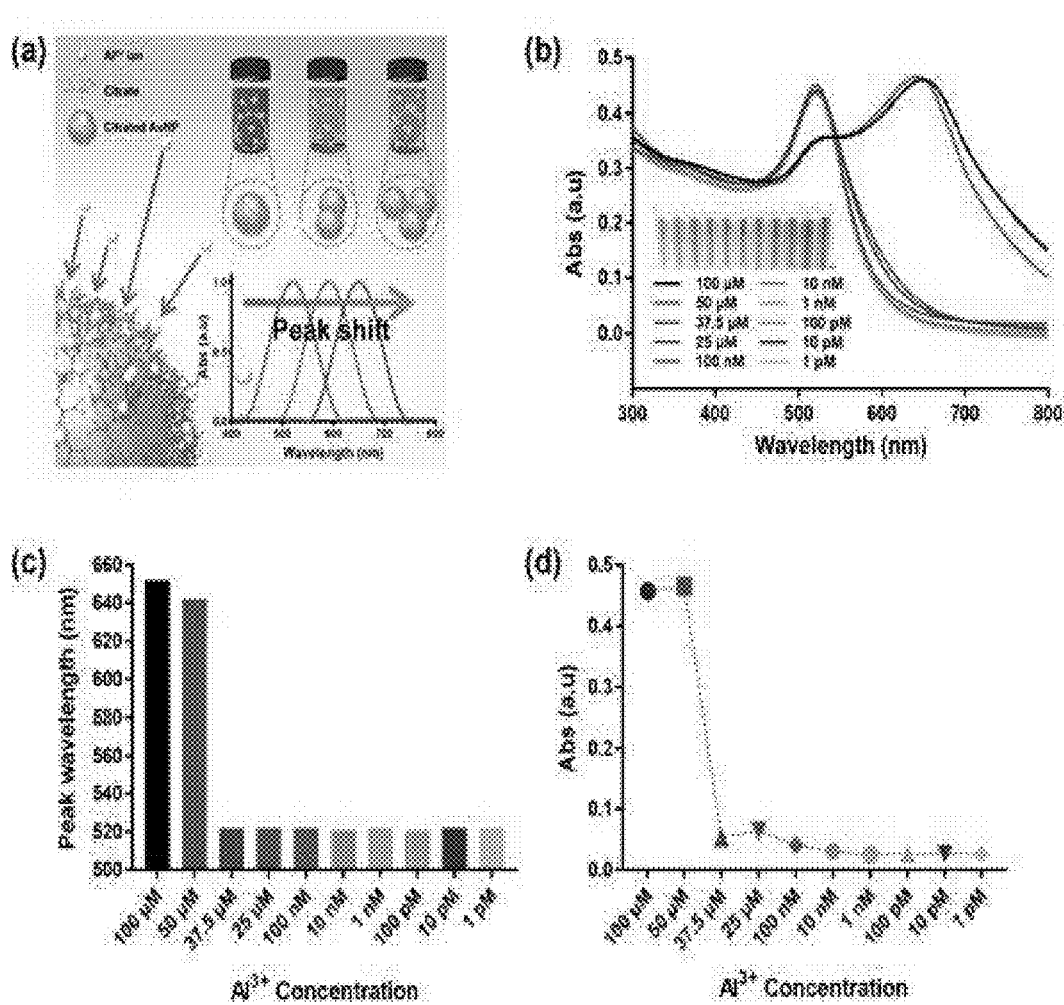
FIGS. 4a, 4b, 4c and 4d show (FIG. 4a) a conceptual diagram showing color changes after aluminum ions are bound to citrated gold nanoparticles, (FIG. 4b) the results of visual observation and UV-VIS spectroscopy for reaction products of gold nanoparticles and aluminum ions at concentrations of 100 µM to 1 pM in a 1:1 ratio, (FIG. 4c) peak wavelengths of the reaction products with aluminum ions at different concentrations, and (FIG. 4d) 640-nm absorbance values of the reaction products with aluminum ions at different concentrations.

FIG. 4 shows (a) a conceptual diagram showing color changes after aluminum ions were bound to the citrated gold nanoparticles and (b) the results of visual observation and UV-VIS spectroscopy for the reaction products of the gold nanoparticles and aluminum ions at concentrations of 100 μM to 1 pM in a 1:1 ratio. As the integration of the gold nanoparticles proceeded through binding with the aluminum ions proceeded, the color of the solution turned red to blue. When the aluminum ion concentration was 50 μM or more, the peak wavelength exceeded 520 nm, which is the background peak wavelength of the gold nanoparticles. Meanwhile, no color change or peak shift was observed when the aluminum ion concentration was less than 50 μM. In FIG. 4, (c) and (d) are graphs showing peak wavelengths and 640-nm absorbance values of the reaction products with aluminum ions at different concentrations, respectively. These graphs show that the gold nanoparticles were not integrated at aluminum ion concentrations of less than 50 μM, as confirmed previously. These results concluded that the naked eye or an optical instrument is not suitable for the detection of aluminum ions at very low concentrations.

Figure 5:
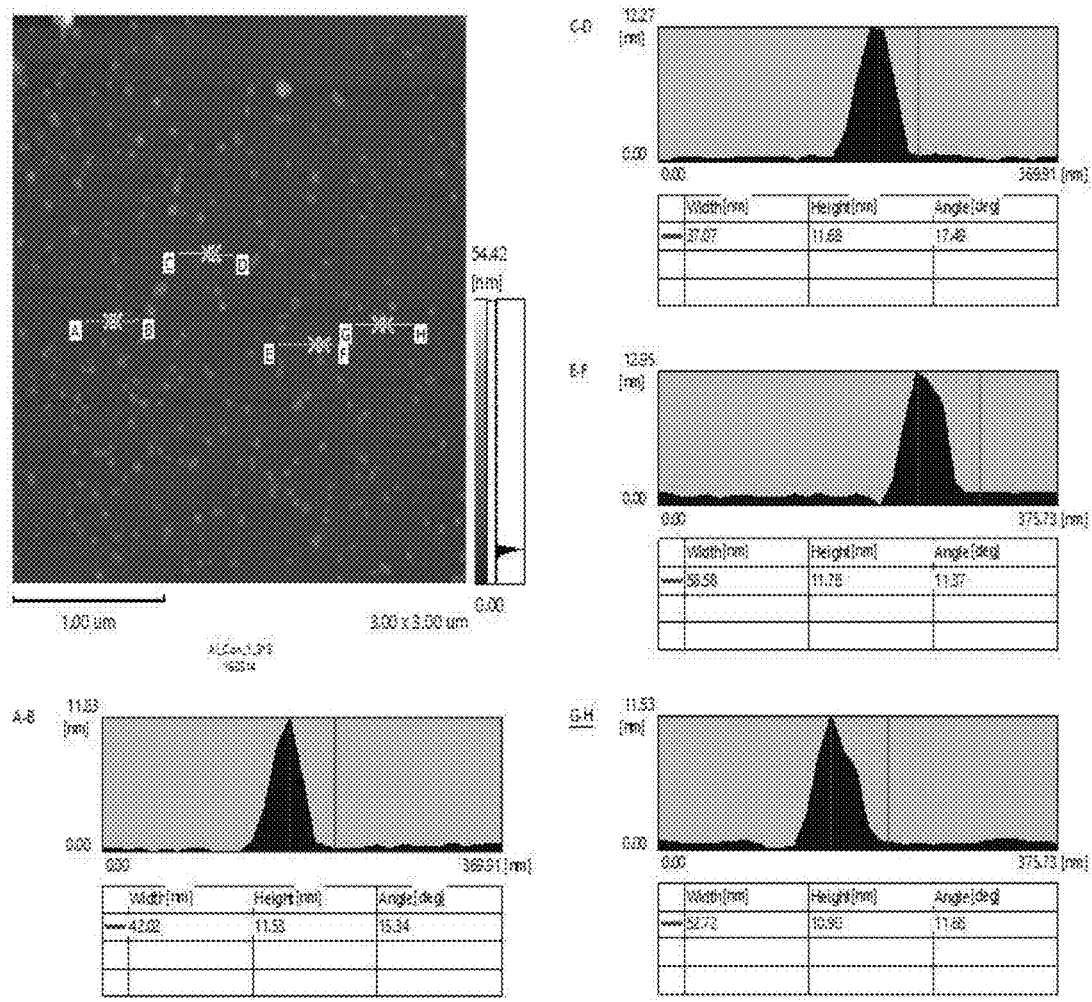
FIG. 5 is an AFM image of bare citrated gold nanoparticles as a control.

Atomic Force Microscopy and Kelvin Probe Force Microscopy (1) First, the bare citrated gold nanoparticles were observed by atomic force microscopy (AFM). FIG. 5 shows the AFM image. Referring to FIG. 5, the AFM analysis reveals that the bare citrated gold nanoparticles were about 15-20 nm in height.

Figure 6:
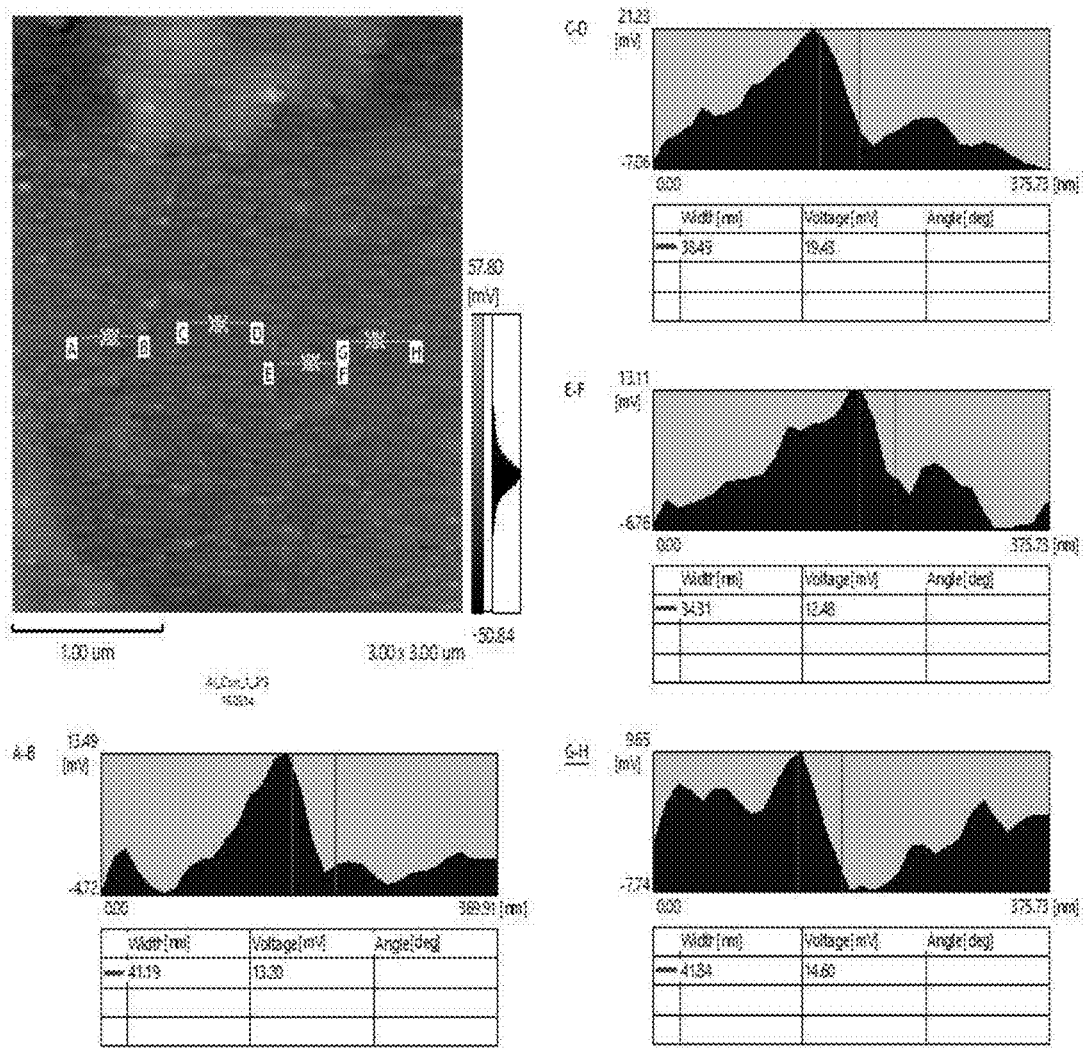
FIG. 6 is a KPFM image of bare citrated gold nanoparticles as a control.

The same area was observed by Kelvin probe force microscopy. The microscopy image shows that the surface of the bare gold nanoparticles was citrated. Since citric acid has terminal carboxyl groups and a hydroxyl group, the citrated gold nanoparticles have negative (−) surface potentials at the edges thereof. FIG. 6 shows the results of KPFM analysis for the bare citrated gold nanoparticles. The bare gold nanoparticles were measured to have a surface potential of ~80 mV.

As described above, tests were conducted on the bare gold nanoparticles as a control. The limit of detection was estimated with decreasing concentration of aluminum ions (100 nM, 10 nM, and 1 nM). Each sample solution containing aluminum ions was added to the solution of the gold nanoparticles to allow the aluminum ions to react with the gold nanoparticles for 2 h. The AFM and KPFM images of the reaction products were analyzed.

Figure 7A:
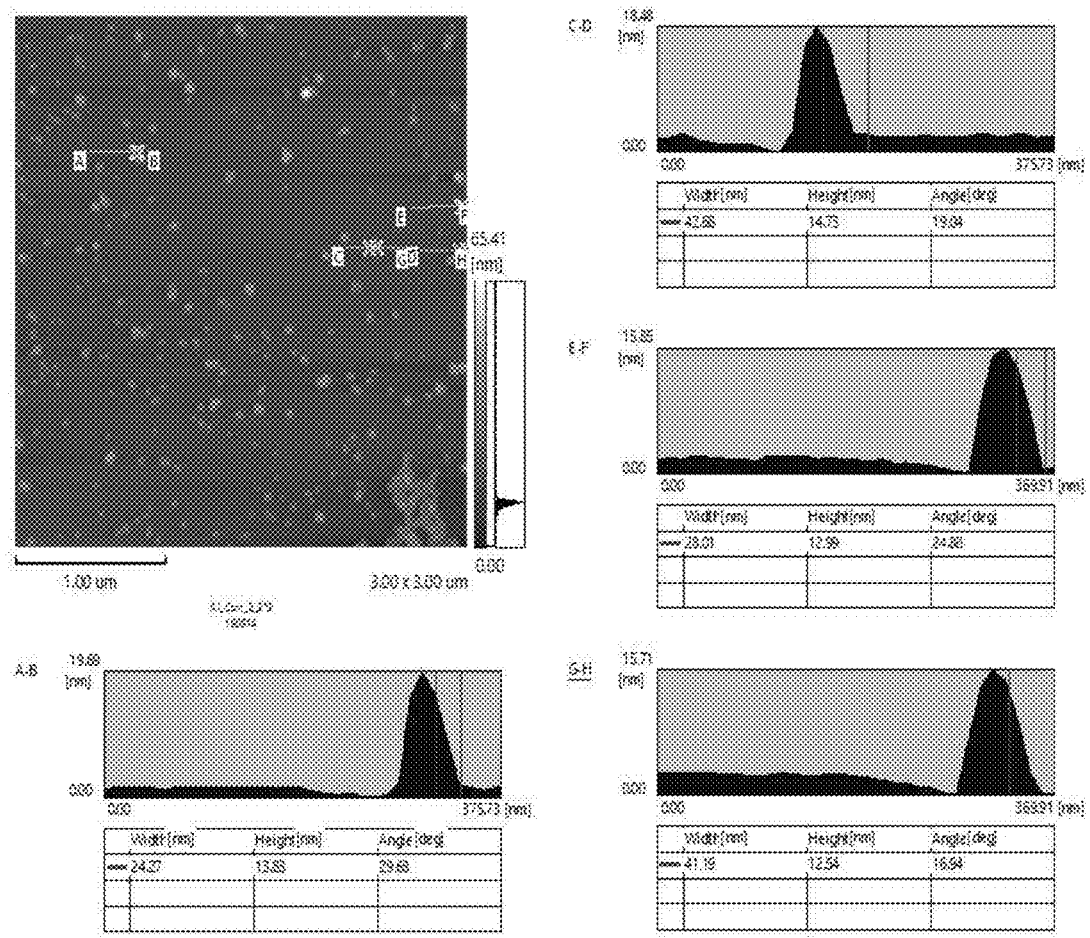
FIGS. 7a and 7b are AFM and KPFM images of a sample containing aluminum ions at a concentration of 100 nM, respectively.
Figure 7B:
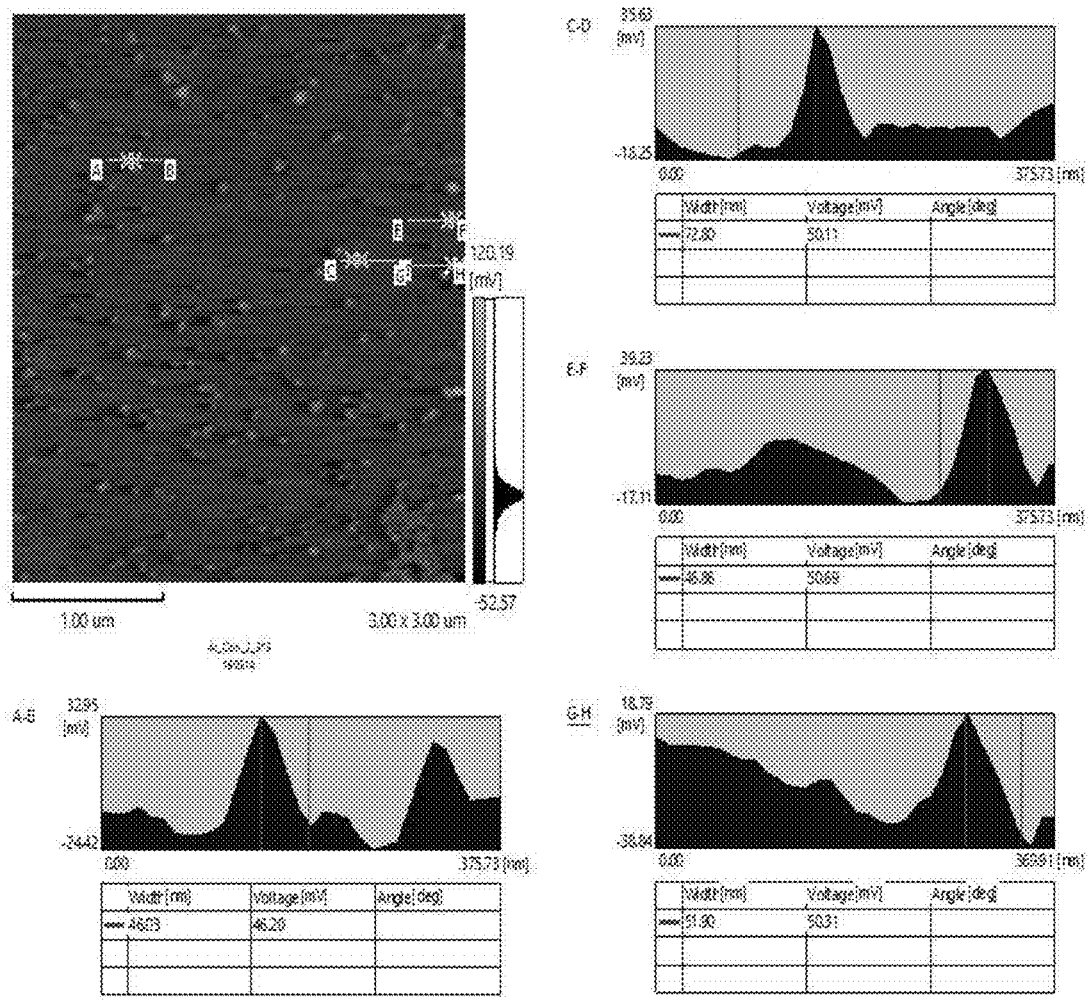

FIGS. 7a and 7b are AFM and KPFM images of the sample containing aluminum ions at a concentration of 100 nM, respectively. The AFM image of FIG. 7a shows that the aluminum ions added at a concentration of 100 nM were bound between the citrate ligands, resulting in integration of the gold nanoparticles that had been separated from each other. This have previously been impossible to visually observe. The KPFM image of FIG. 7b shows that the difference in surface potential between the edge and central portions of the citrated gold nanoparticles was 50 mV, which is different by ~30 mV from that of the bare gold nanoparticle.

Figure 8A:
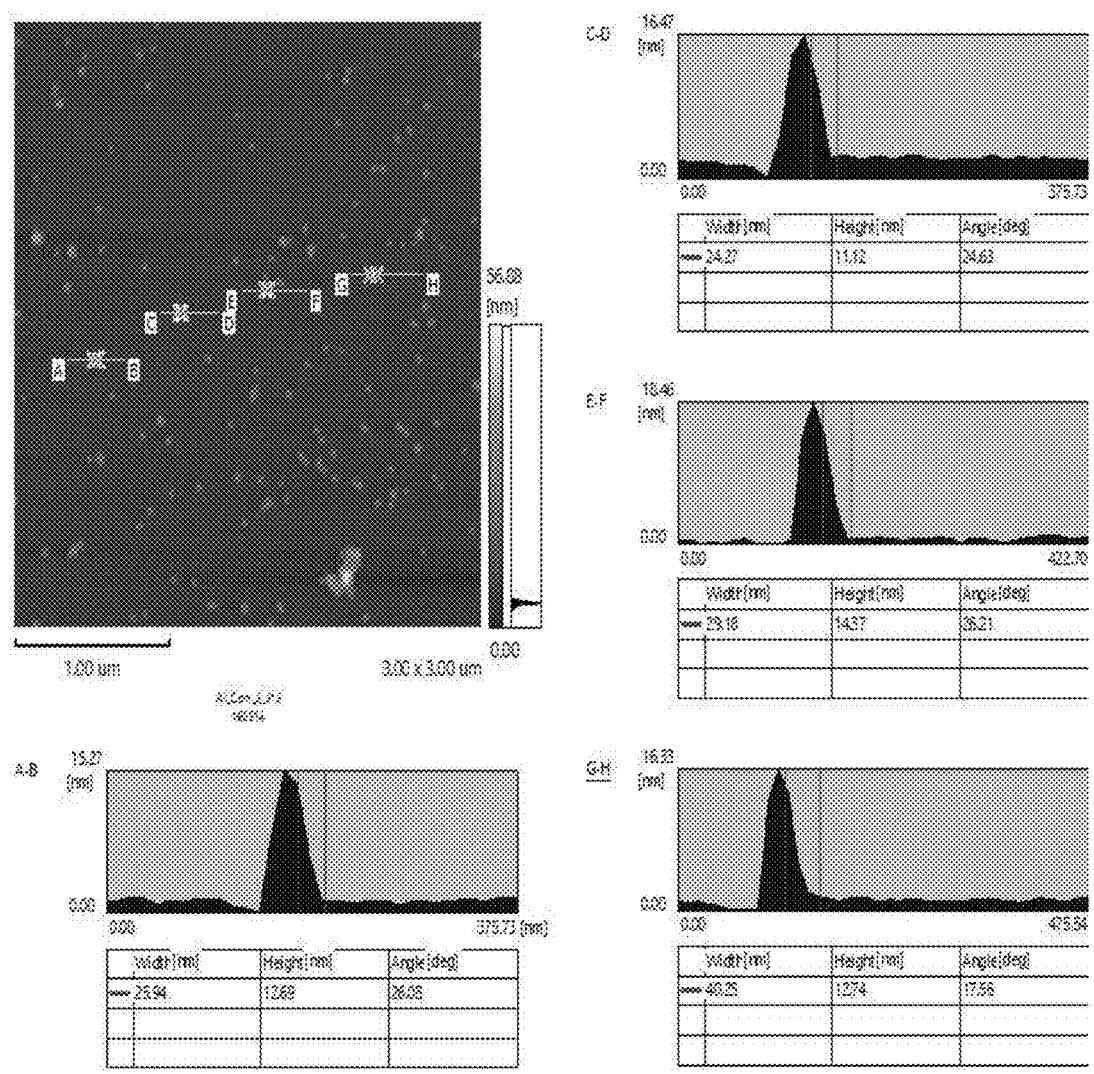
FIGS. 8a and 8b are AFM and KPFM images of a sample containing aluminum ions at a concentration of 10 nM, respectively.
Figure 8B:
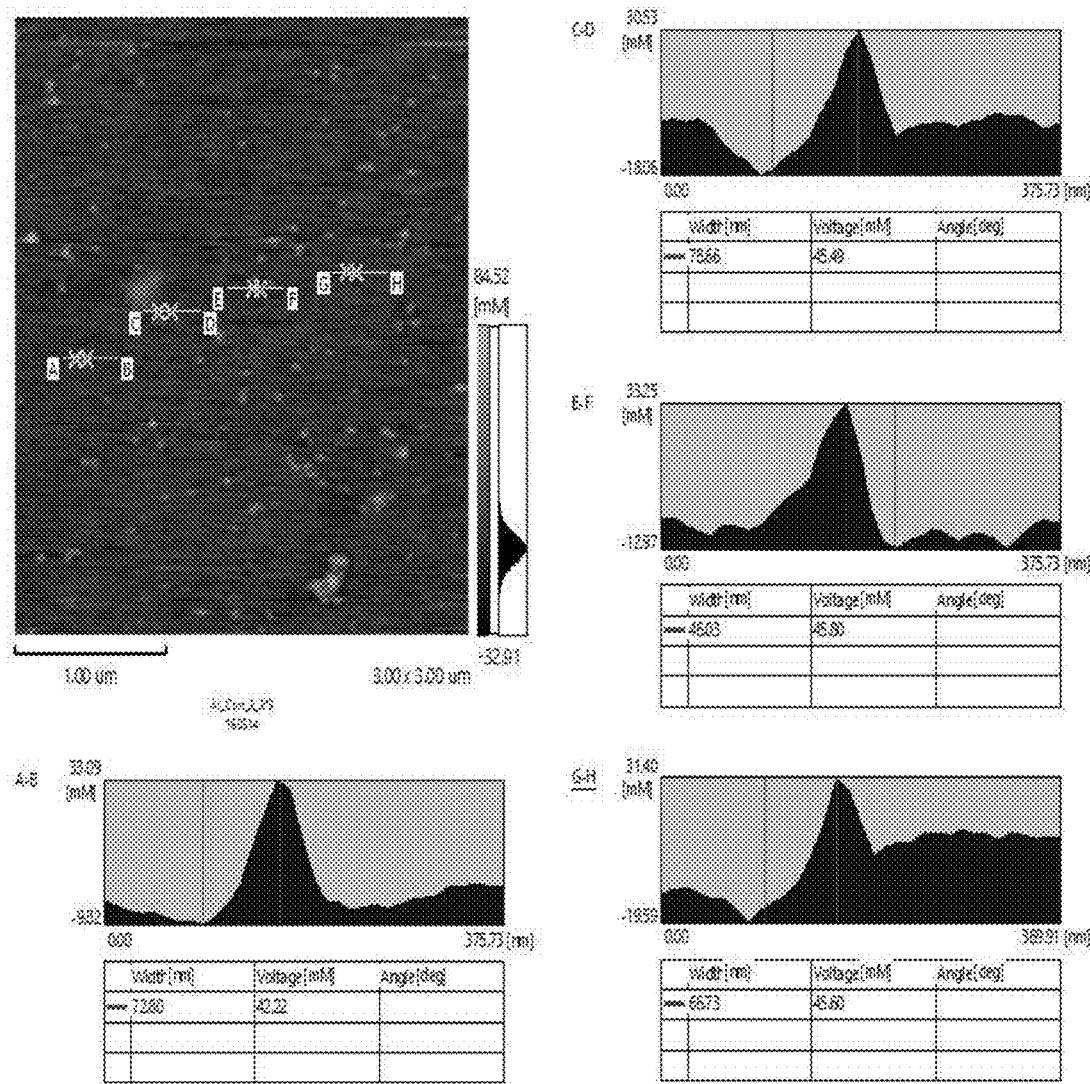

FIGS. 8a and 8b are AFM and KPFM images of the sample containing aluminum ions at a concentration of 10 nM, respectively. The AFM image of FIG. 8a shows that the aluminum ions added at a concentration of 10 nM were bound between the citrate ligands, resulting in integration of the gold nanoparticles that had been separated from each other. The gold nanoparticles were not settled down at the bottom, unlike when the sample containing aluminum ions at a concentration of 100 nM was added. The KPFM image of FIG. 8b shows that the difference in surface potential between the edge and central portions of the citrated gold nanoparticles was 45 mV, which is different by ~25 mV from that of the bare gold nanoparticle.

Figure 9A:
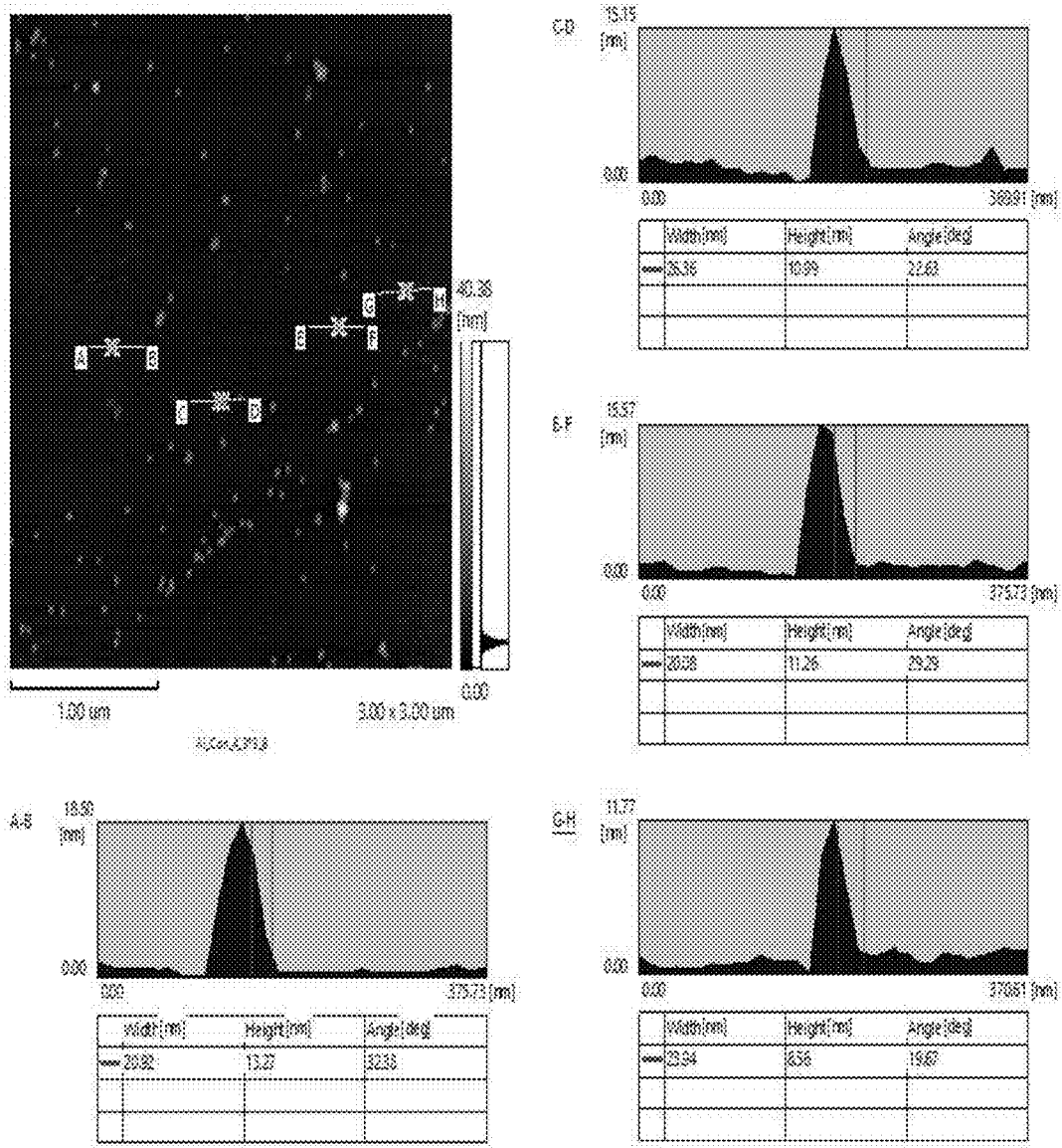
FIGS. 9a and 9b are AFM and KPFM images of a sample containing aluminum ions at a concentration of 1 nM, respectively.
Figure 9B:
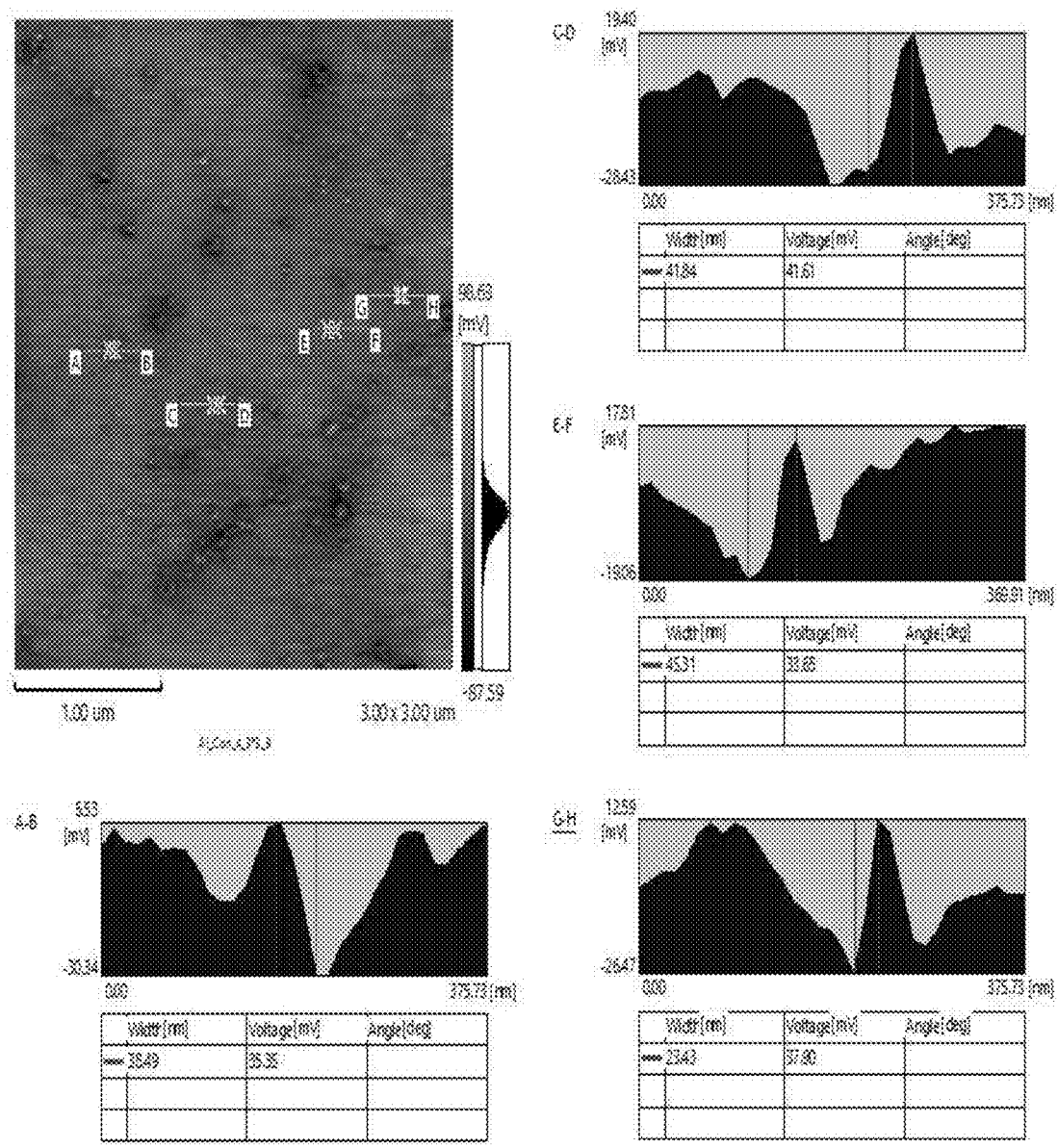

FIGS. 9a and 9b are AFM and KPFM images of the sample containing aluminum ions at a concentration of 1 nM, respectively. The AFM image of FIG. 9a shows that the aluminum ions added at a concentration of 1 nM were bound between the citrate ligands, resulting in integration of the gold nanoparticles that had been separated from each other. However, this integration was almost indiscernible by AFM. Also in the actual image, it was not able to easily identify how the gold nanoparticles were bound to each other. The height of the gold nanoparticle aggregates was 16 nm, which was almost the same as that of the bare gold nanoparticles. The KPFM image of FIG. 9b shows that the difference in surface potential between the edge and central portions of the gold nanoparticles was 40 mV, which is different by ~20 mV from that of the bare gold nanoparticle. That is, even a trace amount of aluminum ions, which had been almost impossible to discern by AFM, could be analyzed by KPFM.

These results collectively suggest that the method of the present invention facilitates the detection of even a trace amount of toxic metal ions, which had been impossible to detect by conventional methods.

Figures 10A, 10B, 10C:
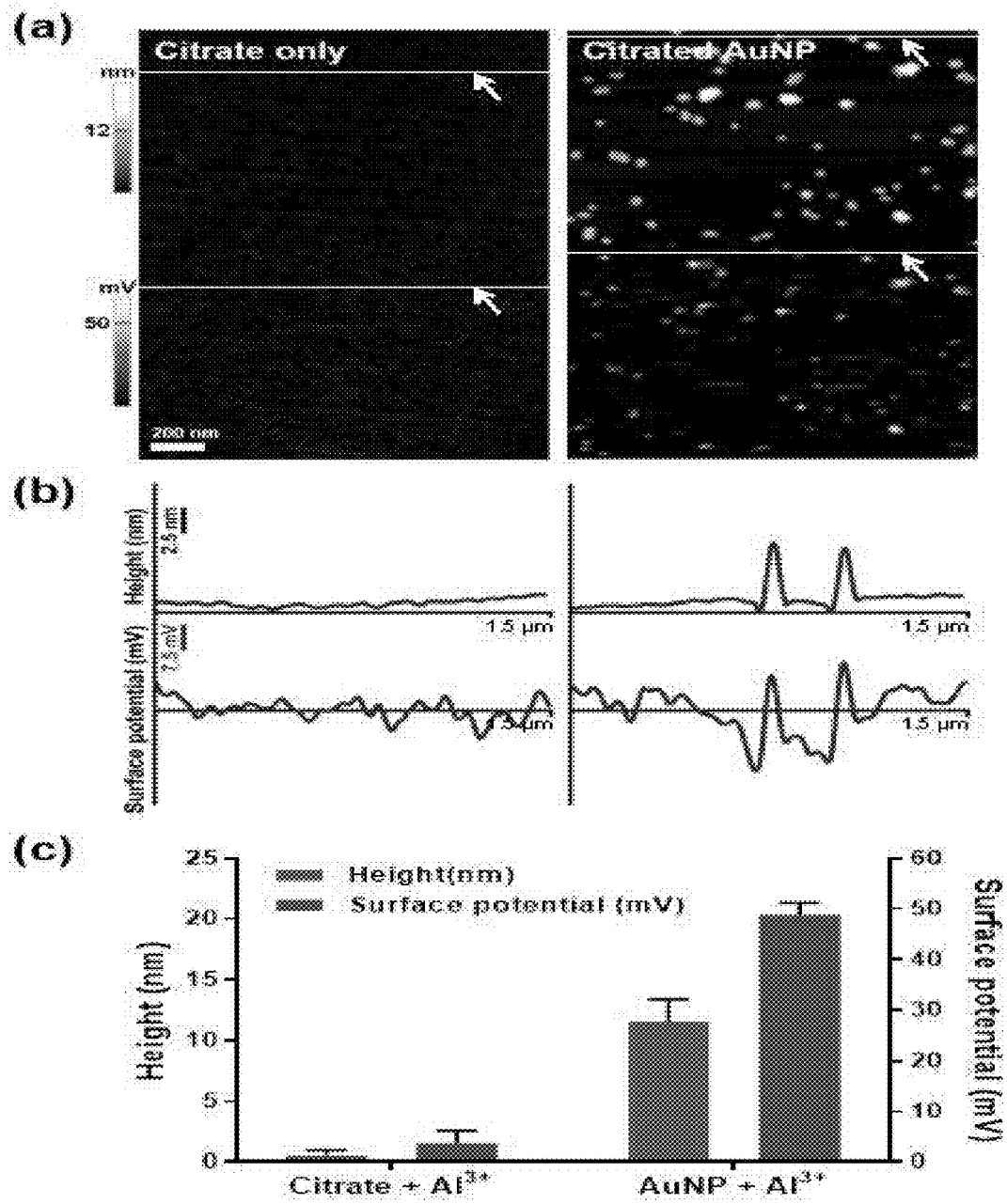
FIGS. 10a, 10b and 10c compare the heights and surface potentials of a reaction product of citrate and a sample containing aluminum ions at a concentration of 100 nM and a reaction product of citrated gold nanoparticles and a sample containing aluminum ions at a concentration of 100 nM, (FIG. 10a): images showing the heights and surface potentials, (FIG. 10b): line profiles of the images of (FIG. 10a), and (FIG. 10c): quantified results of the heights and surface potentials.

(2) In addition, the heights and surface potentials of the reaction product of citrate and the sample containing aluminum ions at a concentration of 100 nM were compared with those of the reaction product of the citrated gold nanoparticles and the sample containing aluminum ions at a concentration of 100 nM. The results are shown in FIG. 10. In FIG. 10, (a) shows images showing the heights and the surface potentials, (b) shows line profiles of the images of (a), and (c) shows quantified results of the heights and surface potentials.

Referring to FIG. 10, when only citrate was used, the sample surface was flat, which makes it difficult to find the locations of the aluminum ions and causes many errors in surface potential values that vary in response to the aluminum ions. In contrast, when the citrated gold nanoparticles were used, the locations of the aluminum ions could be easily found (the locations of the gold nanoparticles have the same meaning as those of the aluminum ions). In addition, it was advantageous to analyze the surface potential due to its large step height. As shown in (c) of FIG. 10, the surface potential was measured to be very high because of the amplification effect of the gold nanoparticles, indicating that the ability to detect the aluminum ions was greatly improved.

Figures 11A, 11B, 11C, 11D, 11E:
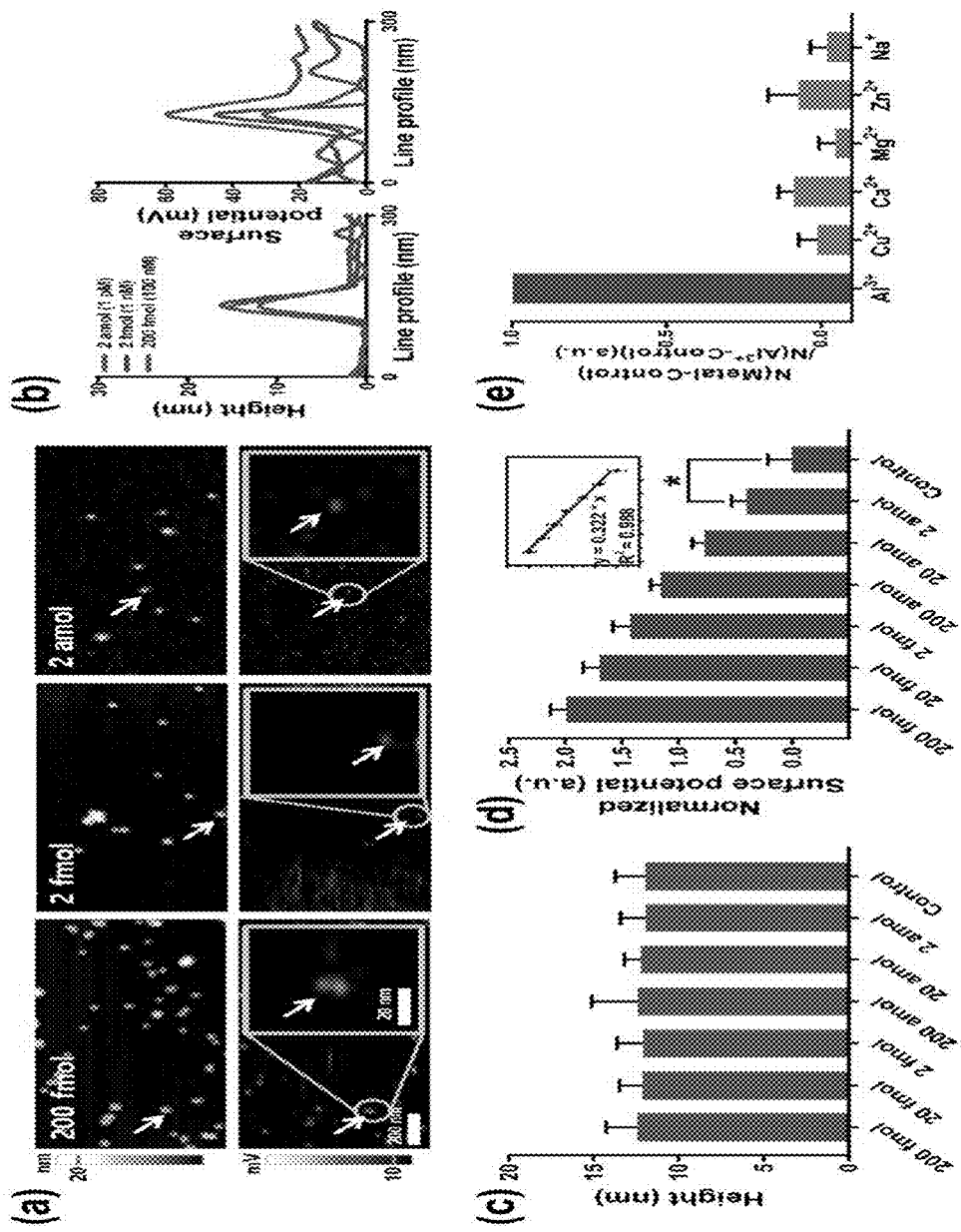
FIGS. 11a, 11b, 11c, 11d and 11e show the heights and surface potentials of reaction products of citrated gold nanoparticles and aluminum ions at different concentrations of 0 (Control), 2 amol (1 pM), 20 amol, 200 amol, 2 fmol, 20 fmol, and 200 fmol, (FIG. 11a): images showing the heights and surface potentials, (FIG. 11b): line profiles of gold nanoparticles marked with arrows in the images of (FIG. 11a), (FIG. 11c): results obtained by quantifying the heights from the images of (FIG. 11a), (FIG. 11d): results obtained by quantifying the surface potentials from the images of (FIG. 11a), and (FIG. 11e): results obtained by comparing the surface potentials of reaction products of citrated gold nanoparticles and various heavy metal ions (copper, calcium, manganese, zinc, and sodium ions) with the surface potential of a reaction product of citrated gold nanoparticles and aluminum ions.

(3) In addition, further tests were conducted whether the use of the citrated gold nanoparticles enables the detection of lower concentrations of aluminum ions. Specifically, the heights and surface potentials of the reaction products of the citrated gold nanoparticles and aluminum ions at concentrations of 0 (Control), 2 amol (1 pM), 20 amol, 200 amol, 2 fmol, 20 fmol, and 200 fmol were analyzed. The results are shown in FIG. 11. In FIG. 11, (a) shows images showing the heights and the surface potentials, (b) shows line profiles of gold nanoparticles marked with arrows in the images of (a), (c) shows the results obtained by quantifying the heights from the images of (a), (d) shows the results obtained by quantifying the surface potentials from the images of (a), and (e) shows the results obtained by comparing the surface potentials of the reaction products of citrated gold nanoparticles and various heavy metal ions (copper, calcium, manganese, zinc, and sodium ions) with the surface potential of the reaction product of citrated gold nanoparticles and aluminum ions.

Referring to FIG. 11, there were no significant differences in the height of the reaction products when the concentrations of the aluminum ions were low, making it impossible to detect the aluminum ions at an ionic level through the height analysis. In contrast, since the size and step height of the surface potential increased with increasing concentration of the aluminum ions, it was possible to detect the aluminum ions at extremely low concentrations (limit of detection=2 amol) through the surface potential analysis (see b, c, and d of FIG. 11). In conclusion, the method of the present invention has the advantages that a reaction product of citrated gold nanoparticles and aluminum ions can be used in an extremely small amount (2 uL) on a silicon wafer, no pretreatment process is required (label-free), unlike when optical instruments and other devices are used, and target ions can be detected with high sensitivity. (e) of FIG. 11 shows the selectivities of the citrated gold nanoparticles for other heavy metal ions. The citrated gold nanoparticles hardly reacted with the heavy metal ions compared to with aluminum ions, demonstrating high selectivity of the citrated gold nanoparticles for the detection of aluminum ions. These results rely on the characteristics of the functional groups attached to the surface of the gold nanoparticles, suggesting that the citrated gold nanoparticles can be optionally imparted with high selectivities for various heavy metal ions by varying the kind of the functional groups.

Figures 12A, 12B, 12C:
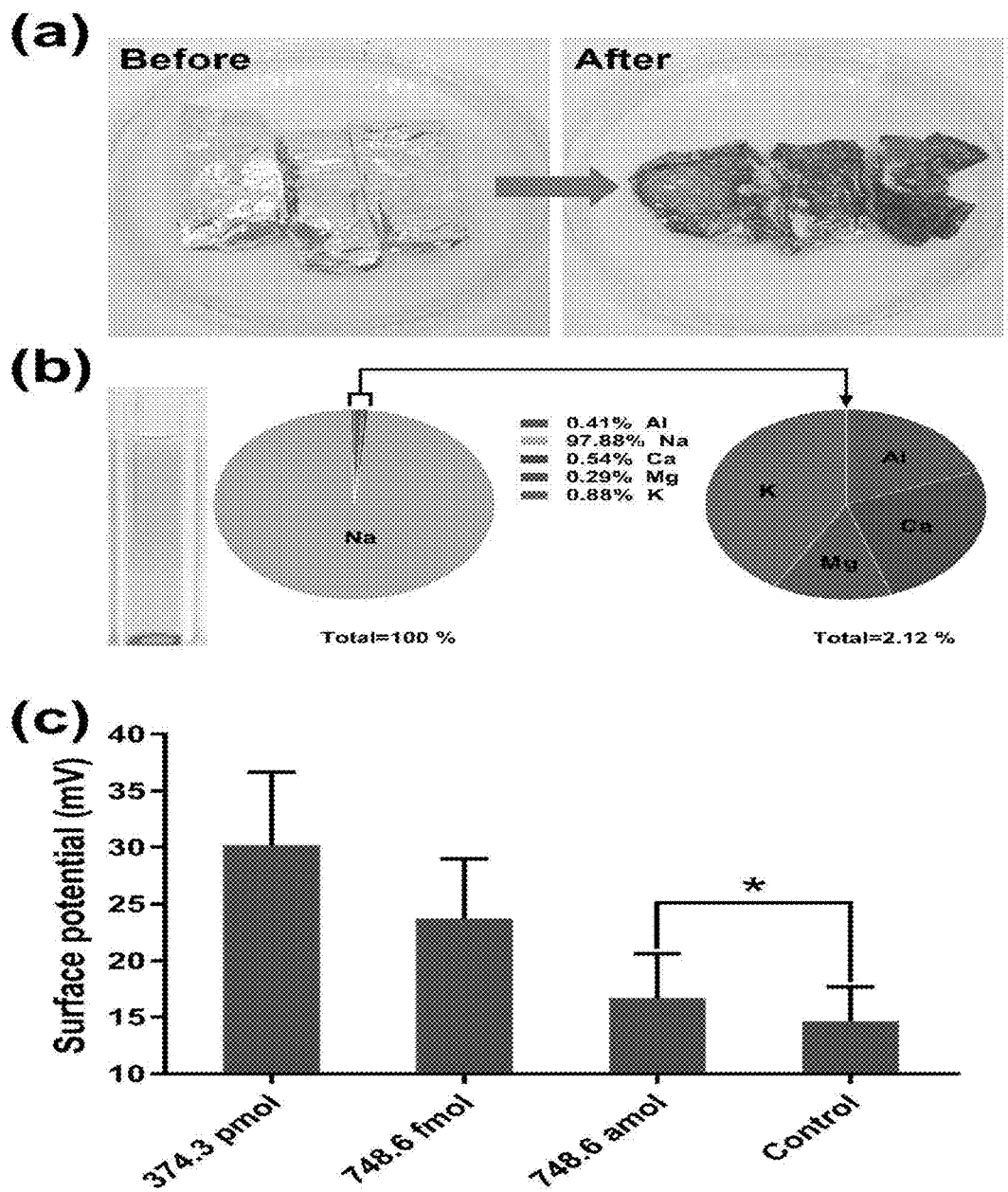
FIGS. 12a, 12b and 12c show test results for the ability of the method of the present invention to detect aluminum ions using an aluminum foil, (FIG. 12a): images of an aluminum foil before and after heating in drinking water containing 1 mM sodium chloride for 30 minutes, (FIG. 12b): results of ICP-MS analysis for a reaction product of aluminum ions remaining in the drinking water after heating and citrated gold nanoparticles in a 1:1 ratio, and (FIG. 12c): detection sensitivity to dilute samples of aluminum ions remaining in the drinking water after heating.

(4) Finally, the ability of the method according to the present invention to detect aluminum ions originating from the actual environment was investigated. To this end, an aluminum foil, which is considered one of the most widely used kitchen items, was used. The results are shown in FIG. 12. In FIG. 12, (a) shows images of an aluminum foil before and after heating in drinking water (Samdasoo, produced by the Jeju Special Self-Governing Province Development Corporation, Korea) containing 1 mM sodium chloride for 30 min, (b) shows the results of ICP-MS analysis for a reaction product of aluminum ions remaining in the drinking water after heating and the citrated gold nanoparticles in a 1:1 ratio, and (c) shows detection sensitivity to dilute samples of aluminum ions remaining in the drinking water after heating.

Referring to (a) of FIG. 12, heating of the aluminum foil in the drinking water containing 1 mM sodium chloride caused a reaction with the base to form a black aluminum oxide film, indicating the presence of aluminum ions in the drinking water. After heating of the aluminum foil, aluminum ions remaining in the drinking water were allowed to react with the citrated gold nanoparticles in a 1:1 ratio. The reaction product was analyzed by ICP-MS. The results are shown in (b) of FIG. 12. As shown in (b) of FIG. 12, the aluminum ions were integrated with the gold nanoparticles, and as a result, the reaction product of the gold nanoparticles and the aluminum ions was precipitated. Other ions, such as potassium, calcium, and sodium ions, were also detected. The reason for the high sodium content was because the aluminum foil was heated in the presence of 1 mM sodium chloride in the drinking water. Aluminum was not included in the minerals of the drinking water before heating but was found in the drinking water after heating, demonstrating that the aluminum was derived from the aluminum foil. Next, the heated drinking water was diluted and the detection sensitivity was examined. The results are shown in (c) of FIG. 12. Referring to (c) of FIG. 12, aluminum ions were detected by surface potential microscopy using the citrated gold nanoparticles (2 uL). The limit of detection was found to be 748.6 amol, confirming that the method of the present invention enables the detection of aluminum ions from actual environmental samples (such as drinking water samples and water supply and drainage samples) with very high sensitivity.

In conclusion, according to the method of the present invention, even a trace amount of toxic metal ions in a sample can be detected with high sensitivity. Therefore, the method of the present invention can be applied to the management of water quality in food service providers and hospitals, the measurement of contaminants in water supply and drainage systems, and the management of industrial wastewater. Furthermore, the method of the present invention is expected to be widely applicable to water purifiers and the food and beverage industry in the future.

What is claimed is:

1. A method for detecting toxic metal ions in a sample, comprising:
    a) preparing a solution of organic acid-bound gold nanoparticles;
    b) adding a sample containing toxic metal ions to the solution prepared in a) to form a reaction solution and to allow the gold nanoparticles to aggregate in the reaction solution;
    c) dropping the reaction solution obtained in b) onto a silicon substrate and drying the reaction solution such that a gold nanoparticle aggregate is immobilized on the silicon substrate to form a sample substrate;
    d) measuring a height of the gold nanoparticle aggregate immobilized on the sample substrate by atomic force microscopy; and
    e) detecting the toxic metal ions in the sample by comparing the height of the gold nanoparticle aggregate immobilized on the sample substrate with a height of a gold nanoparticle aggregate immobilized on a control substrate prepared from a control without the toxic metal ions.

2. The method according to claim 1, wherein the organic acid is selected from the group consisting of citric acid, cytosine, thymine, and mixtures thereof.

3. The method according to claim 1, wherein the toxic metal ions are ions of at least one metal selected from the group consisting of aluminum, mercury, silver, and copper.

4. The method according to claim 1, wherein the gold nanoparticles are allowed to aggregate at room temperature for 1.5 hours to 3 hours.

5. The method according to claim 1, wherein a concentration of the toxic metal ions in the sample is less than 1 µM.

6. A method for detecting toxic metal ions in a sample, comprising:
    a) preparing a solution of organic acid-bound gold nanoparticles;
    b) adding a sample containing toxic metal ions to the solution prepared in a) to form a reaction solution and to allow the gold nanoparticles to aggregate in the reaction solution;
    c) dropping the reaction solution obtained in b) onto a silicon substrate and drying the reaction solution such that a gold nanoparticle aggregate is immobilized on the silicon substrate to form a sample substrate;
    d) measuring a surface potential of the gold nanoparticle aggregate immobilized on the sample substrate by Kelvin probe force microscopy; and
    e) detecting the toxic metal ions in the sample by comparing the surface potential of the gold nanoparticle aggregate immobilized on the sample substrate with a surface potential of a gold nanoparticle aggregate immobilized on a control substrate prepared from a control without the toxic metal ions.

7. The method according to claim 6, wherein the organic acid is selected from the group consisting of citric acid, cytosine, thymine, and mixtures thereof.

8. The method according to claim 6, wherein the toxic metal ions are ions of at least one metal selected from the group consisting of aluminum, mercury, silver, and copper.

9. The method according to claim 6, wherein the gold nanoparticles are allowed to aggregate at room temperature for 1.5 hours to 3 hours.

10. The method according to claim 6, wherein a difference between the surface potential of the gold nanoparticle aggregate immobilized on the sample substrate and the surface potential of the gold nanoparticle aggregate immobilized on the control substrate increases in proportion to the concentration of the toxic metal ions in the sample.

11. The method according to claim 6, wherein a concentration of the toxic metal ions in the sample is less than 1 µM.

* * * * *